United States Patent [19]

Doria et al.

[11] 4,428,952

[45] Jan. 31, 1984

[54] SUBSTITUTED PYRROLO[2,1-B]QUINAZOLINES AND PYRIDO[2,1-B]QUINAZOLINES USEFUL FOR THE TREATMENT OF OR THE PREVENTION OF GASTROINTESTINAL ULCERS

[75] Inventors: Gianfederico Doria, Milan; Carlo Passarotti, Gallarate; Giuliana Arcari, Milan, all of Italy

[73] Assignee: Farmitalia Carlo Erba S.p.A., Milan, Italy

[21] Appl. No.: 387,181

[22] Filed: Jun. 10, 1982

[30] Foreign Application Priority Data

Jun. 30, 1981 [GB] United Kingdom ............... 8120126

[51] Int. Cl.$^3$ .................. A61K 31/505; C07D 471/04
[52] U.S. Cl. ...................................... 424/251; 542/442; 544/252
[58] Field of Search ................. 424/251; 542/442; 544/252

[56] References Cited

U.S. PATENT DOCUMENTS

| 3,271,396 | 9/1966 | Bernstein et al. | 544/252 |
| 3,558,610 | 1/1971 | Breuer et al. | 542/442 X |
| 4,123,533 | 10/1978 | Hermecz et al. | 542/442 X |
| 4,310,526 | 1/1982 | Doria et al. | 424/251 X |

FOREIGN PATENT DOCUMENTS 2739020 3/1979 Fed. Rep. of Germany.
52-77093 6/1977 Japan.

OTHER PUBLICATIONS

Arndt et al., Chemical Abstracts, vol. 67, 73732h, (1967).
Kametani et al., Chemical Abstracts, vol. 78, 97850y, (1973).
Kametani et al., Chemical Abstracts, vol. 82, 4452q, (1975).
Kametani et al., Chemical Abstracts, vol. 82, 16864p, (1975).
Shakhidoyatov et al., Chemical Abstracts, vol. 88, 7166j, (1978).
Johne et al., Chemical Abstracts, vol. 89, 24589n, (1978).
Bergner et al., Chemical Abstracts, vol. 89, 101913t, (1978).
Shakhidoyatov et al., Chemical Abstracts, vol. 94, 192253v, (1981).
Sharma et al., Chemical Abstracts, vol. 97, 6605a, (1982).

Primary Examiner—Donald G. Daus
Assistant Examiner—Diana G. Rivers
Attorney, Agent, or Firm—Murray and Whisenhunt

[57] ABSTRACT

Substituted Pyrrolo [2,1-b] and Pyrido [2, 1 b] Quinazolines are provided, together with pharmaceutical compositions, containing them. The compounds have pharmaceutical utility, and are particularly useful for the treatment of or prevention of the formation of gastrointestinal ulcers.

14 Claims, No Drawings

SUBSTITUTED PYRROLO[2,1-B]QUINAZOLINES AND PYRIDO[2,1-b]QUINAZOLINES USEFUL FOR THE TREATMENT OF OR THE PREVENTION OF GASTROINTESTINAL ULCERS

The present invention relates to substituted pyrrolo[2,1-b] and pyrido[2,1-b]quinazolines, to a process for their preparation and to pharmaceutical compositions containing them. The invention provides compounds having the following general formula (I)

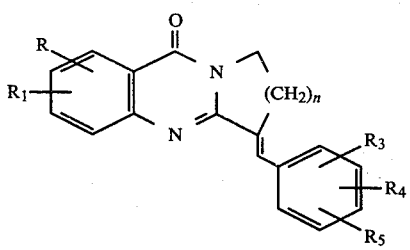

wherein n is 1 or 2; each of

R and $R_2$ independently represents: (a) a hydrogen or a halogen atom; (b) a $C_1$–$C_4$ alkyl group, a —$CH_2OH$ group or a cyano group; (c) a carboxy group or a group —$COOR_6$, wherein $R_6$ represents a $C_1$–$C_6$ alkyl group which may be unsubstituted or substituted by $C_1$–$C_4$ dialkylamino group; (d) a group

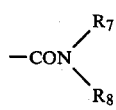

wherein each of $R_7$ and $R_8$ independently represents a hydrogen atom or a $C_1$–$C_4$ alkyl group; (e) amino, a $C_2$–$C_6$ alkanoylamino group or a formylamino group, at least one of R and $R_1$ being different from hydrogen when n is 1;

$R_2$ represents a hydrogen atom or a $C_1$–$C_4$ alkyl group;

each of $R_3$, $R_4$ and $R_5$ independently represents a hydrogen or a halogen atom, a hydroxy group, formyloxy, a $C_2$–$C_8$ alkanoyloxy group, a —$CF_3$ group, a $C_1$–$C_4$ alkyl group, a $C_1$–$C_4$ alkoxy group or a $C_3$–$C_4$ alkenyloxy group or adjacent groups represented by two of $R_3$, $R_4$ and $R_5$, taken together, form a $C_1$–$C_3$ alkylenedioxy group; and the pharmaceutically acceptable salts thereof.

The invention also includes within its scope all the possible isomers, stereoisomers and optical isomers and their mixtures, and the metabolites and the metabolic precursors of the compounds of formula (I).

The numbering used to identify the position in the compounds of formula (I) is the conventional one, as is depicted in the following examples:

(A) when n = 1:

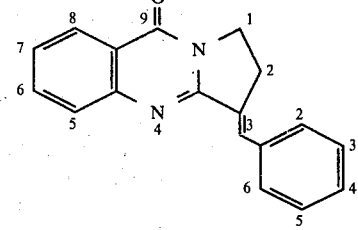

(B) when n = 2:

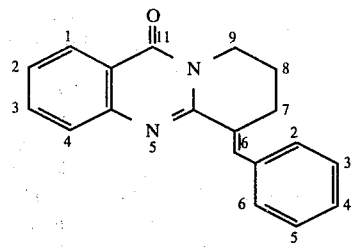

When $R_6$ is an unsubstituted $C_1$–$C_6$ alkyl group it is preferably methyl, ethyl, isopropyl, hexyl or n-butyl.

Preferably $R_2$ is hydrogen or a methyl group.

When R and/or $R_1$ is a $C_1$–$C_4$ alkyl group, it is preferably methyl.

When R and/or $R_1$ is a halogen atom, it is preferably chlorine.

When one or more or $R_3$, $R_4$ and $R_5$ are halogen, the halogen is preferably chlorine or fluorine.

When one or more of $R_3$, $R_4$ and $R_5$ are $C_1$–$C_4$ alkyl, the alkyl groups are preferably methyl or ethyl.

When one or more of $R_3$, $R_4$ and $R_5$ are $C_1$–$C_4$ alkoxy, the alkoxy groups are preferably methoxy or ethoxy.

The alkyl, alkoxy and alkanoyloxy groups may be branched or straight chain groups.

A $C_2$–$C_6$ alkanoylamino group is preferably an acetylamino group.

A $C_2$–$C_8$ alkanoyloxy group is preferably an acetoxy group.

Preferred compounds of the invention are the compounds of formula (I) wherein n is 1 or 2; R is hydrogen; $R_1$ is chlorine, cyano, hydroxymethyl, methyl, amino, carboxy, $C_1$–$C_4$ alkoxycarbonyl, di($C_1$–$C_2$ alkyl)-amino-ethoxycarbonyl or aminocarbonyl; $R_2$ is hydrogen or methyl; each of $R_3$, $R_4$ and $R_5$ independently represents hydrogen, $C_1$–$C_2$ alkyl, $C_1$–$C_3$ alkoxy, fluorine, chlorine or adjacent groups represented by two of $R_3$, $R_4$ and $R_5$, taken together, form a methylenedioxy group; and the pharmaceutically acceptable salts thereof.

Examples of pharmaceutically acceptable salts are either those with inorganic bases, such as sodium, potassium, calcium and aluminium hydroxides or with organic bases, such as lysine, triethylamine, triethanolamine, dibenzylamine, methylbenzylamine, di-(2-ethylhexyl)-amine, piperidine, N-ethylpiperidine, N,N-diethylaminoethylamine, N-ethylmorpholine, β-phenethylamine, N-benzyl-β-phenethylamine, N-benzyl-N,N-dimethylamine and the other acceptable organic amines, as well as the salts with inorganic acids, e.g. hydrochloric, hydrobromic sulphuric and nitric acids and with organic acids, e.g. citric, tartaric, maleic, malic, fumaric, methanesulphonic and ethanesulphonic acids.

Preferred salts are the sodium and the potassium salts, as well as the hydrochlorides of the basic esters, e.g. the diethylaminoethyl and dimethylaminoethyl esters.

Examples of particularly preferred compounds of the invention are:

3-benzylidene-1,2,3,9-tetrahydro-9-oxo-pyrrolo[2,1-b]quinazoline-7-carboxylic acid;

3-(2-methyl-benzylidene)-1,2,3,9-tetrahydro-9-oxo-pyrrolo[2,1-b]quinazoline-7-carboxylic acid;

3-benzylidene-1,2,3,9-tetrahydro-9-oxo-pyrrolo[2,1-b]quinazoline-6-carboxylic acid;

3-(3-methyl-benzylidene)-1,2,3,9-tetrahydro-9-oxo-pyrrolo[2,1-b]quinazoline-7-carboxylic acid;

3-(2-methyl-benzylidene)-1,2,3,9-tetrahydro-9-oxo-pyrrolo[2,1-b]quinazoline-6-carboxylic acid;

3-benzylidene-1-methyl-1,2,3,9-tetrahydro-9-oxo-pyrrolo[2,1-b]quinazoline-7-carboxylic acid;

3-benzylidene-1-methyl-1,2,3,9-tetrahydro-9-oxo-pyrrolo[2,1-b]quinazoline-6-carboxylic acid;

6-benzylidene-6,7,8,9-tetrahydro-11-oxo-11H-pyrido[2,1-b]quinazoline-2-carboxylic acid;

6-(2-methyl-benzylidene)-6,7,8,9-tetrahydro-11-oxo-11H-pyrido[2,1-b]quinazoline-2-carboxylic acid;

6-benzylidene-6,7,8,9-tetrahydro-11-oxo-11H-pyrido[2,1-b]quinazoline-3-carboxylic acid;

6-(2-methyl-benzylidene)-6,7,8,9-tetrahydro-11-oxo-11H-pyrido[2,1-b]quinazoline-3-carboxylic acid;

3-benzylidene-7-chloro-1,2,3,9-tetrahydro-pyrrolo[2,1-b]quinazoline-9-one;

7-chloro-3-(2-methyl-benzylidene)-1,2,3,9-tetrahydro-pyrrolo[2,1-b]quinazoline-9-one;

3-benzylidene-6-chloro-1,2,3,9-tetrahydro-pyrrolo[2,1-b]quinazoline-9-one;

6-chloro-3-(2-methyl-benzylidene)-1,2,3,9-tetrahydro-pyrrolo[2,1-b]quinazoline-9-one;

7-amino-3-benzylidene-1,2,3,9-tetrahydro-pyrrolo[2,1-b]quinazoline-9-one;

6-amino-3-benzylidene-1,2,3,9-tetrahydro-pyrrolo[2,1-b]quinazoline-9-one;

6-amino-3-benzylidene-1-methyl-1,2,3,9-tetrahydro-pyrrolo[2,1-b]quinazoline-9-one;

3-amino-6-benzylidene-6,7,8,9-tetrahydro-11H-pyrido[2,1-b]quinazoline-11-one;

3-benzylidene-1,2,3,9-tetrahydro-9-oxo-pyrrolo[2,1-b]quinazoline-6-carboxylic acid, ethyl ester;

3-benzylidene-1,2,3,9-tetrahydro-9-oxo-pyrrolo[2,1-b]quinazoline-6-carboxylic acid, 2-diethylaminoethyl ester;

6-benzylidene-6,7,8,9-tetrahydro-11-oxo-11H-pyrido[2,1-b]quinazoline-3-carboxylic acid, ethyl ester, as well as the pharmaceutically acceptable salts thereof, in particular the sodium salts of the carboxylic acids and the hydrochlorides of the basic esters (e.g. those with 2-diethylamino-ethanol) and the $C_1$–$C_6$ alkyl esters thereof, in particular the methyl, ethyl, isopropyl, n-butyl and n-hexyl esters.

The compounds of the invention can be prepared by a process comprising:

(a) reacting a compound of formula (II)

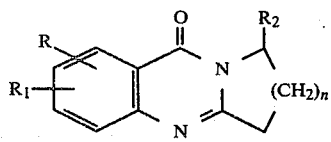

(II)

wherein n, R, $R_1$ and $R_2$ are as defined above or a salt thereof, with an aldehyde of formula (III)

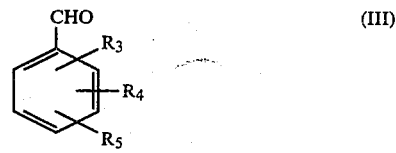

(III)

wherein $R_3$, $R_4$ and $R_5$ are as defined above; or (b) reducing a compound of formula (Ia)

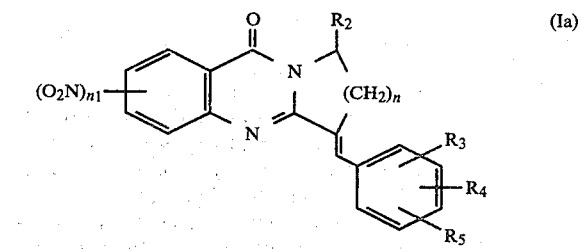

(Ia)

wherein n, $R_2$, $R_3$, $R_4$ and $R_5$ are as defined above, and $n_1$ is 1 or 2, so obtaining a compound of formula (I) wherein R and/or $R_1$ are amino; and/or, if desired, converting a compound of formula (I) into another compound of formula (I) and/or, if desired, converting a compound of formula (I) into a pharmaceutically acceptable salt and/or, if desired, converting a salt into a free base or into a free acid; and/or, if desired, resolving a mixture of isomers into the single isomers.

The reaction of a compound of formula (II) with an aldehyde of formula (III) is preferably carried out in the presence of basic condensing agents such as piperidine, sodium ethoxide, sodium methoxide, sodium hydride, sodium amide or sodium hydroxide, in a solvent such as methanol, ethanol, dioxane or water or their mixtures, at a temperature preferably ranging from about 0° C. to about 120° C.

The reduction of a compound of formula (Ia) may be carried out, for example, by treatment with stannous chloride in concentrated hydrochloric acid, using if necessary an organic cosolvent such as acetic acid, dioxane, tetrahydrofuran, at a temperature varying between room temperature and the reflux temperature, preferably between room temperature and about 60° C.

A compound of formula (I) may be converted, as stated above, into another compound of formula (I) by known methods; for example, the compound of formula (I) wherein $R_1$ is an esterified carboxy group, may be converted into a compound of formula (I) wherein $R_1$ is carboxy by hydrolysis, e.g. basic hydrolysis, using, for example, sodium or potassium hydroxide, in a solvent, such as, water, lower aliphatic alcohols or their mixtures, and operating at a temperature ranging from room temperature to about 150° C.; the same reaction may be also carried out e.g. by treatment with lithium bromide in dimethylformamide at a temperature higher than 50° C. or by treatment with hydrochloric or hydrobromic or hydroiodic or sulphuric acid in acetic acid at temperature higher than 50° C.

A compound of formula (I) wherein $R_1$ is carboxy may be converted into a compound of formula (I)

wherein $R_1$ is an esterified carboxy group, e.g. a carbalkoxy group unsubstituted or substituted by a lower dialkylamino group, by conventional methods, for example by reacting an alkaline salt of the acid with a suitable alkyl halide, in an inert solvent, such as, acetone, dioxane dimethylformamide or hexamethylphosphorotriamide, at a temperature ranging from about 0° C. to about 100° C.

A compound of formula (I) wherein $R_1$ is amino may be converted into a compound of formula (I) wherein $R_1$ is formylamino or $C_2$-$C_6$ alkanoylamino, for example by reaction with formic acid or with the corresponding alkanoyl anhydride without a solvent or in an organic solvent such as dioxane, dimethylformamide, tetrahydrofuran, usually in the presence of a base such as pyridine or triethylamine, at a temperature varying between 0° C. and about 100° C. Alternatively the esterification of a compound of formula (I) may be effected by:

(a) converting the compound of formula (I) wherein $R_1$ is carboxy into the corresponding halocarbonyl, preferably chlorocarbonyl, derivative, by reaction, e.g. with the desired acid halide, for example oxalyl chloride, thionyl chloride, $PCl_3$, $PCl_5$ or $POCl_3$, either in the absence of solvents or in an inert organic solvent such as, benzene, toluene, xylene, dioxane, dichloroethane, methylene chloride or tetrahydrofurane, at a temperature ranging preferably from about 0° C. to about 120° C.; and then (b) reacting the resulting halocarbonyl derivative with a suitable alcohol of formula $R_6$-OH, wherein $R_6$ is as defined above, in an inert solvent such as, benzene, toluene, xylene, dioxane, dichloroethane, methylene chloride or tetrahydrofurane, at temperatures varying from about 0° C. to about 120° C., preferably in the presence of a base, such as, triethylamine or pyridine.

A compound of formula (I), wherein $R_1$ is carboxy, may be converted into a compound of formula (I), wherein $R_1$ is a

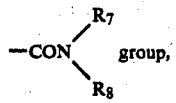 group, wherein $R_7$ and $R_8$ are as above defined, by known methods, for example, by converting the carboxy group into the corresponding halide, preferably the chloride, by reaction, e.g., with thionyl chloride in benzene or dioxane or dichloroethane, at a temperature ranging from room temperature to about 100° C., then by reacting the halide with ammonia or a suitable alkyl amine of formula

wherein $R_7$ and $R_8$ are as above defined, at room temperature in one of the above mentioned solvents.

A compound of formula (I) wherein $R_1$ is a —$CONH_2$ group may be converted into a compound of formula (I) wherein $R_1$ is a —CN group, by dehydrating the amide, e.g., by means of p-toluensulphonyl chloride in pyridine and dimethylformamide at a temperature ranging from room temperature to about 100° C.

A compound of formula (I) wherein $R_1$ is an esterified or unesterified carboxy group may be converted into a compound of formula (I) wherein $R_1$ is a —$CH_2OH$ group, by treatment with a reducing agent such as $LiAlH_4$ in an inert solvent such as dioxane, tetrahydrofurane or diglyme, at a temperature from about 0° C. to about 30° C.

Free hydroxy groups may be, for example, etherified by reacting with a suitable alkyl halide in the presence of a base such as NaOH, KOH, $Na_2CO_3$, $K_2CO_3$, NaH, $NaNH_2$, sodium methoxide or sodium ethoxide, in a solvent such as methanol, ethanol, dioxane, acetone, dimethylformamide, hexamethylphosphorotriamide, tetrahydrofurane or water or their mixtures at a temperature ranging preferably from about 0° C. to about 150° C. Furthermore the etherified hydroxy groups may be converted into free hydroxy groups, for example, by treatment with pyridine hydrochloride or with a strong acid such as, HCl, HBr or HI, or with a Lewis acid such as, $AlCl_3$ or $BBr_3$.

Also the optional salification of a compound of formula (I) as well as the conversion of a salt into the free compound and the separation of a mixture of isomers into the single isomers may be carried out by conventional methods.

For example the separation of a mixture of optical isomers into the individual isomers may be carried out by salification with an optically active base and subsequent fractional crystallization.

The compounds of formula (II) may, for example, be prepared by reacting a compound of formula (IV)

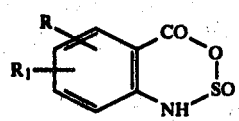

wherein
R and $R_1$ as defined above, with a compound of formula (V)

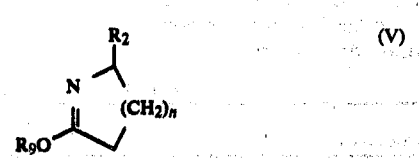

wherein
n and $R_2$ are as defined above and $R_9$ represents a hydrogen atom or a $C_1$-$C_6$ alkyl group. The reaction between a compound of formula (IV) and a compound of formula (V) may, for example, be carried out in an inert organic solvent such as benzene, toluene, dioxane or tetrahydrofurane at a temperature varying from about 0° C. to about 50° C., preferably at room temperature.

The compounds of formula (IV), which generally are not isolated because of their low chemical stability, may be prepared for example by reacting a compound of formula (VI)

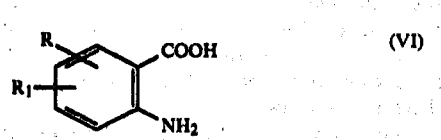

wherein

R and $R_1$ are as defined above, with $SOCl_2$ at a temperature varying from room temperature to about 100° C., in an inert solvent such as benzene, toluene, dioxane or dichloroethane.

The compounds of formula (Ia) may be prepared by reacting compounds of formula (IIa)

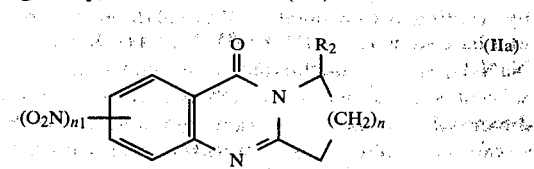

wherein $n_1$, n and $R_2$ are as defined above with an aldehyde of formula (III), following the same reaction conditions described above for process (a).

The compounds of formulae (III), (V) and (VI) are known compounds and are commercially available products or may be obtained by methods known in organic chemistry.

The compounds of the present invention are active on the gastroenterical system, in particular they are endowed with anti-ulcerogenic and anti-secretory activity and are therefore useful in therapy, for example in the prevention and treatment of peptic, e.g. duodenal, gastric and esophageal ulcers and to inhibit gastric acid secretion. The compounds of the invention are also useful for reducing the undesirable gastrointestinal side-effects resulting from systemic administration of anti-inflammatory prostaglandin synthetase inhibitors and may be, therefore, used for this purpose in association with them.

The anti-ulcerogenic activity of the compounds of the invention is shown, e.g., by the fact that they are active in the test of the inhibition of restraint ulcers in rats, according to the method of Bonfils et al., (Thérapie, 1960, 5, 1096; Jap. J. Pharmac. 1945, 43, 5).

The following Table shows, for example, the approximate $ED_{50}$ value of the anti-ulcerogenic activity in the rat obtained for some compounds of the invention after oral administration:

TABLE

| Compound | Anti-ulcerogenic activity $ED_{50}$ p.o. |
|---|---|
| 3-benzylidene-1,2,3,9-tetrahydro-9-oxo-pyrrolo[2,1-b]quinazoline-7-carboxylic acid | 8 mg/kg |
| 3-benzylidene-1,2,3,9-tetrahydro-9-oxo-pyrrolo[2,1-b]quinazoline-6-carboxylic acid | 10 mg/kg |
| 6-benzylidene-6,7,8,9-tetrahydro-11-oxo-11H-pyrido[2,1-b]quinazoline-2-carboxylic acid | 9 mg/kg |
| 6-benzylidene-6,7,8,9-tetrahydro-11-oxo-11H-pyrido[2,1-b]quinazoline-3-carboxylic acid | 8 mg/kg |

The tested compound was administered per os (p.o.) one hour before the immobilization. Six Sprague-Dawley male rats (100–120 g) fasted 24 hours were used for the experiment: a square flexible small-mesh wire netting was used for the immobilization and 4 hours after the immobilization the rats were sacrificed, their stomachs were removed and the lesions counted under a dissecting microscope.

The compounds of the invention own also antisecretory activity as shown, e.g., by the fact that they proved to be active after intraduodenal administration in inhibiting the gastric secretion in rats according to the method of H. Shay et al. (Gastroenter., 1945, 43, 5).

For example, as regards the antisecretory activity the compound 6-benzylidene-6,7,8,9-tetrahydro-11-oxo-11H-pyrido/2,1-b/quinazoline-3-carboxylic acid has an approximate $ED_{50}$ value of 15 mg/kg after intraduodenal administration in rats according to the above method.

Considering that many anti-ulcer agents display, as does atropine, a remarkable but undesired anti-cholinergic activity, the compounds of the invention have been assessed for their antagonism against syndrome induced by oxotremorine in mice, according to the method described by Leszkovszky G. P. and Tardos L. (Europ. J.Pharmac. 1971, 15, 310).

Following this test the compounds of the invention have been found devoid of anticholinergic activity; for example the compounds:
3-benzylidene-1,2,3,9-tetrahydro-9-oxo-pyrrolo[2,1-b]quinazoline-7-carboxylic acid;
3-benzylidene-1,2,3,9-tetrahydro-9-oxo-pyrrolo[2,1-b]quinazoline-6-carboxylic acid;
6-benzylidene-6,7,8,9-tetrahydro-11-oxo-11H-pyrido[2,1-b]quinazoline-2-carboxylic acid;
6-benzylidene-6,7,8,9-tetrahydro-11-oxo-11H-pyrido[2,1-b]quinazoline-3-carboxylic acid,
are inactive in the above test at a dose of 100 mg/kg after oral administration.

In view of their high therapeutic index the compounds of the invention can be safely used in medicine. For example, the approximate acute toxicity ($LD_{50}$) of the compounds 3-benzylidene-1,2,3,9-tetrahydro-9-oxo-pyrrolo[2,1-b]quinazoline-7-carboxylic acid; 3-benzylidene-1,2,3,9-tetrahydro-9-oxo-pyrrolo[2,1-b]quinazoline-6-carboxylic acid; 6-benzylidene-6,7,8,9-tetrahydro-11-oxo-11H-pyrido[2,1-b]quinazoline-2-carboxylic acid; 6-benzylidene-6,7,8,9-tetrahydro-11-oxo-11H-pyrido[2,1-b]quinazoline-3-carboxylic acid in mouse, determined with single administration of increasing doses and measured on the seventh day of treatment is per os higher than 800 mg/kg.

Analogous toxicity data have been found for the other compounds of the invention.

The compounds of the invention can be administered in a variety of dosage forms, e.g. orally, in the form of tablets, capsules, sugar or film coated tablets, liquid solution or suspensions, rectally, in the form of suppositories, parenterally, e.g. intramuscularly, or by intravenous injection or infusion.

The dosage depends on the age, weight, conditions of the patient and administration route; for example the dosage adopted for oral administration to adult humans ranges from 50 to 200 mg pro dose, from 1 to 5 times daily.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form. For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g.

starches, arabic gums, gelatin, methylcellulose, carboxymethyl cellulose or polyvinyl pyrrolidone; disaggregating agents, e.g. a starch, alginic acid, alginates or sodium starch glycolate; effervescing mixtures; dyestuff sweeteners; wetting agents, such as, lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes. The liquid dispersions for oral administration may be e.g. syrups, emulsions and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g. sterile isotonic aqueous saline solution, olive oil, ethyl oleate, glycols, e.g. propylene glycol, and if desired, a suitable amount of lidocaine hydrochloride. The solutions for intravenous injections or infusions may contain as carrier, for example, sterile water or preferably they may be in the form of sterile aqueous isotonic saline solutions. The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

4-amino-isophthalic acid (27 g), dry methanol (500 ml) and conc. $H_2SO_4$ (27 ml) were heated at 60° C. for 20 hours; after cooling the reaction mixture was concentrated in vacuo and the residue was diluted with ice-water. The precipitate was filtered and partitioned between chloroform and 5% $NaHCO_3$, the aqueous phase was separated, acidified with 37% HCl and the precipitate was collected by filtration and washed with water until neutral: the resulting 4-amino-benzene-1,3-dicarboxylic acid, 1-methyl ester, m.p. 224°-227° C. (19.5 g) was reacted with $SOCl_2$ (18 ml) in benzene (300 ml) at the reflux temperature for 3 hours. The solution was evaporated in vacuo to dryness and the residue was dissolved in dioxane (300 ml) and reacted with 2-pyrrolidinone (10.2 g) at room temperature for 20 hours. The precipitate was filtered, washed with dioxane and then treated with aqueous $NaHCO_3$ to give, after filtration and washing with water until neutral, 13.5 g of 1,2,3,9-tetrahydro-9-oxo-pyrrolo[2,1-b]quinazoline-7-carboxylic acid, methyl ester, m.p. 197°-200° C., which was reacted with benzaldehyde (17.5 g) in methanol (500 ml) in the presence of sodium methoxide (6 g) under stirring at 60° C. for 3 hours. After cooling the precipitate was filtered, washed with methanol and water until neutral to give 14.8 g of 3-benzylidene-1,2,3,9-tetrahydro-9-oxo-pyrrolo[2,1-b]quinazoline-7-carboxylic acid, methyl ester, m.p. 253°-256° C., which was heated in a mixture of 37% HCl-acetic acid 1:1 (325 ml) at the reflux temperature for 5 hours to give 12.7 g of 3-benzylidene-1,2,3,9-tetrahydro-9-oxo-pyrrolo[2,1-b]quinazoline-7-carboxylic acid, m.p. 285°-287° C. NMR ($CF_3COOD$)δ: 2.58 (s) (3H, $CH_3$), 3.66 (m) (2H, C-2 protons) 4.74 (t) (2H, C-1 protons), 7.40-7.85 (m) (4H, phenyl protons), 8.09 (d) (1H, C-5 proton), 8.65 (t) (1H, methine proton), 8.84 (d d) (1H, C-6 proton), 9.30 (d) (1H, C-8 proton) p.p.m.

By proceeding analogously, using the suitable substituted benzaldehydes, the following compounds were prepared:

3-(3-methyl-benzylidene)-1,2,3,9-tetrahydro-9-oxo-pyrrolo[2,1-b]quinazoline-7-carboxylic acid, m.p. 319°-321° C.;

3-(4-methyl-benzylidene)-1,2,3,9-tetrahydro-9-oxo-pyrrolo[2,1-b]quinazoline-7-carboxylic acid, m.p. 340°-350° C. dec.;

3-(2,5-dimethyl-benzylidene)-1,2,3,9-tetrahydro-9-oxo-pyrrolo[2,1-b]quinazoline-7-carboxylic acid, m.p. 302°-305° C.;

3-(2,4-dimethyl-benzylidene)-1,2,3,9-tetrahydro-9-oxo-pyrrolo[2,1-b]quinazoline-7-carboxylic acid, m.p. 310°-312° C.;

3-(3-methoxy-benzylidene)-1,2,3,9-tetrahydro-9-oxo-pyrrolo[2,1-b]quinazoline-7-carboxylic acid, m.p. 325°-327° C.;

3-(3,-chlorobenzylidene)-1,2,3,9-tetrahydro-9-oxo-pyrrolo[2,1-b]quinazoline-7-carboxylic acid, m.p. 328°-330° C.;

3-(2,6-dichlorobenzylidene)-1,2,3,9-tetrahydro-9-oxo-pyrrolo[2,1-b]quinazoline-7-carboxylic acid, m.p. 298°-300° C.;

3-(2-methoxy-benzylidene)-1,2,3,9-tetrahydro-9-oxo-pyrrolo[2,1-b]quinazoline-7-carboxylic acid;

3-(2-methyl-benzylidene)-1,2,3,9-tetrahydro-9-oxo-pyrrolo[2,1-b]quinazoline-7-carboxylic acid, m.p. 285°-287° C.;

3-(2,4-dichloro-benzylidene)-1,2,3,9-tetrahydro-9-oxo-pyrrolo[2,1-b]quinazoline-7-carboxylic acid, m.p. 342°-345° C.;

3-(3,4-dichloro-benzylidene)-1,2,3,9-tetrahydro-9-oxo-pyrrolo[2,1-b]quinazoline-7-carboxylic acid; and 3-(4-fluoro-benzylidene)-1,2,3,9-tetrahydro-9-oxo-pyrrolo[2,1-b]quinazoline-7-carboxylic acid, m.p. 330° C. dec.

EXAMPLE 2

2-amino-5-chloro-benzoic acid (7.3 g) was reacted with $SOCl_2$ (9 ml) in benzene (50 ml) at the reflux temperature for 3 hours. The solution was evaporated in vacuo to dryness and the residue was dissolved in benzene (100 ml) and reacted with 2-pyrrolidinone (4.26 g) at room temperature for 20 hours. The precipitate was filtered, washed with benzene and then treated with aqueous $NaHCO_3$ to give, after filtration and washing with water until neutral, 5.1 g of 7-chloro-1,2,3,9-tetrahydro-pyrrolo[2,1-b]quinazoline-9-one, m.p. 173°-175° C., which was reacted with benzaldehyde (7.2 g) in methanol (120 ml) in the presence of sodium methoxide (2.46 g) under stirring at room temperature for 20 hours. The precipitate was filtered and washed with methanol and then with water until neutral. Crystalization from ethanol gave 4.2 g of 3-benzylidene-7-chloro-1,2,3,9-tetrahydro-pyrrolo[2,1-b]quinazoline-9-one, m.p. 225°-227° C., NMR ($CDCl_3+CF_3COOD$)δ: 3.32 (d t) (2H, C-2 protons), 4.33 (t) (2H, C-1 protons), 7.4-7.7 (m) (5H, phenyl protons), 7.68 (d) (2H, C-5 and C-6 protons), 7.88 (t) (1H, =CH—), 8.28 (t) (C-8 proton) ppm.

By proceeding analogously the following compounds were prepared:

7-chloro-3-(2-methyl-benzylidene)-1,2,3,9-tetrahydro-pyrrolo[2,1-b]quinazoline-9-one, m.p. 227°–230° C.;
7-chloro-3-(3-methyl-benzylidene)-1,2,3,9-tetrahydro-pyrrolo[2,1-b]quinazoline-9-one, m.p. 222°–224° C.;
7-chloro-3-(4-methyl-benzylidene)-1,2,3,9-tetrahydro-pyrrolo[2,1-b]quinazoline-9-one;
7-chloro-3-(2,4-dimethyl-benzylidene)-1,2,3,9-tetrahydro-pyrrolo[2,1-b]quinazoline-9-one;
7-chloro-3-(4-fluoro-benzylidene)-1,2,3,9-tetrahydro-pyrrolo[2,1-b]quinazoline-9-one, m.p. 220°–230° C. dec;
7-chloro-3-(2,6-dichloro-benzylidene)-1,2,3,9-tetrahydro-pyrrolo[2,1-b]quinazoline-9-one, m.p. 208°–209° C.
7-chloro-3-(2,5-dimethyl-benzylidene)-1,2,3,9-tetrahydro-pyrrolo[2,1-b]quinazoline-9-one;
7-chloro-3-(2-methoxy-benzylidene)-1,2,3,9-tetrahydro-pyrrolo[2,1-b]quinazoline-9-one, m.p. 241°–242° C.;
7-chloro-3-(3-methoxy-benzylidene)-1,2,3,9-tetrahydro-pyrrolo[2,1-b]quinazoline-9-one, m.p. 205°–206° C.;
7-chloro-3-(4-methoxy-benzylidene)-1,2,3,9-tetrahydro-pyrrolo[2,1-b]quinazoline-9-one;
7-chloro-3-(2,3-dimethoxy-benzylidene)-1,2,3,9-tetrahydro-pyrrolo[2,1-b]quinazoline-9-one;
7-chloro-3-(3-ethoxy-2-methoxy-benzylidene)-1,2,3,9-tetrahydro-pyrrolo[2,1-b]quinazline-9-one;
7-chloro-3-(2,5-dimethoxy-benzylidene)-1,2,3,9-tetrahydro-pyrrolo[2,1-b]quinazoline-9-one;
7-chloro-3-(3,4-dimethoxy-benzylidene)-1,2,3,9-tetrahydro-pyrrolo[2,1-b]quinazoline-9-one, m.p. 220°–222° C.;
7-chloro-3-(3,4-methylenedioxy-benzylidene)-1,2,3,9-tetrahydro-pyrrolo[2,1-b]quinazoline-9-one;
7-chloro-3-(2,3,4-trimethoxy-benzylidene)-1,2,3,9-tetrahydro-pyrrolo[2,1-b]quinazoline-9-one, m.p. 232°–233° C.;
7-chloro-3-(2,4,5-trimethoxy-benzylidene)-1,2,3,9-tetrahydro-pyrrolo[2,1-b]quinazoline-9-one, m.p. 285°–286° C.;
7-chloro-3-(3,4,5-trimethoxy-benzylidene)-1,2,3,9-tetrahydro-pyrrolo[2,1-b]quinazline-9-one, m.p. 228°–229° C.;
7-chloro-3-benzylidene-1-methyl-1,2,3,9-tetrahydro-pyrrolo[2,1-b]quinazoline-9-one.

EXAMPLE 3

4-amino-benzene-1,3-dicarboxylic acid, 1-methyl ester (12 g), prepared according to Example 1, was reacted with SOCl$_2$ (9 ml) in benzene (200 ml) at the reflux temperature for 3 hours. The solution was evaporated in vacuo to dryness and the residue was dissolved in benzene (160 ml) and reacted with 2-piperidone (7.4 g) at room temperature for 20 hours.

The precipitate was filtered, purified with acetone and then treated with aqueous NaHCO$_3$ to give, after filtration and washing with water until neutral, 6 g of 6,7,8,9-tetrahydro-11-oxo-11H-pyrido[2,1-b]quinazoline-2-carboxylic acid, methyl ester, m.p. 135°–137° C., which was reacted with benzaldehyde (4.8 g) in methanol (100 ml) in the presence of sodium methoxide (3.72 g) under stirring at the reflux temperature for 72 hours.

After cooling the reaction mixture was concentrated in vacuo and then acidified with 37% HCl: the precipitate was filtered, washed with water until neutral and crystallized from chloroform-ethanol to give 2.9 g of 6-benzylidene-6,7,8,9-tetrahydro-11-oxo-11H-pyrido[2,1-b]quinazoline-2-carboxylic acid, m.p. 288°–290° C., NMR (CF$_3$COOD)δp.p.m.: 2.37 (m) (2H, C-8 protons), 3.28 (m) (2H, C-7 protons), 4.46 (m) (2H, C-9 protons), 7.69 (s) (5H, phenyl protons), 8.12 (d) (1H, C-4 proton), 8.20 (s) (1H, =CH—), 8.86 (dd) (1H, C-3 proton), 9.30 (s) (1H, -C1 proton).

By proceeding analogously the following compounds were prepared:

6-(2-methyl-benzylidene)-6,7,8,9-tetrahydro-11-oxo-11H-pyrido[2,1-b]quinazoline-2-carboxylic acid, m.p. 240°–241° C.;
6-(4-methyl-benzylidene)-6,7,8,9-tetrahydro-11-oxo-11H-pyrido[2,1-b]quinazoline-2-carboxylic acid;
6-(2-methoxy-benzylidene)-6,7,8,9-tetrahydro-11-oxo-11H-pyrido[2,1-b]quinazoline-2-carboxylic acid;
6-(3-methyl-benzylidene)-6,7,8,9-tetrahydro-11-oxo-11H-pyrido[2,1-b]quinazoline-2-carboxylic acid;
6-(3-chloro-benzylidene)-6,7,8,9-tetrahydro-11-oxo-11H-pyrido[2,1-b]quinazoline-2-carboxylic acid, m.p. 264°–266° C.;
6-(2,6-dichloro-benzylidene)-6,7,8,9-tetrahydro-11-oxo-11H-pyrido[2,1-b]quinazoline-2-carboxylic acid, m.p. 340° C. dec.;
6-(3-methyl-benzylidene)-6,7,8,9-tetrahydro-11-oxo-11H-pyrido[2,1-b]quinazoline-2-carboxylic acid, and
6-(4-fluoro-benzylidene)-6,7,8,9-tetrahydro-11-oxo-11H-pyrido[2,1-b]quinazoline-2-carboxylic acid, m.p. 294°–296° C.

EXAMPLE 4

1,2,3,9-tetrahydro-9-oxo-pyrrolo[2,1-b]quinazoline-7-carboxylic acid (1.4 g) was reacted with 2-methyl-benzaldehyde (1.65 g) in methanol (50 ml) in the presence of sodium methoxide (1.3 g) under stirring at the reflux temperature for 48 hours. After cooling the reaction mixture was acidified with 37% HCl and the precipitate was filtered and washed with water until neutral: crystallization from chloroform-ethanol gave 1.2 g of 3-(2-methyl-benzylidene)-1,2,3,9-tetrahydro-9-oxo-pyrrolo[2,1-b]quinazoline-7-carboxylic acid, m.p. 285°–287° C., NMR (CF$_3$COOD) δp.p.m.: 2.58 (s) (3H, CH$_3$), 3.66 (m) (2H, C-2 protons), 4.74 (t) (2H, C-1 protons), 7.40–7.85 (m) (4H, phenyl protons), 8.09 (d) (1H, C-5 proton), 8.65 (t) (1H, =CH—), 8.84 (d d) (1H, C-6 proton), 9.30 (d) (1H, C-8 proton).

By proceeding analogous the following compound was prepared:

6-(2-methyl-benzylidene)-6,7,8,9-tetrahydro-11-oxo-11H-pyrido[2,1-b]quinazoline-2-carboxylic acid, m.p. 240°–241° C.

EXAMPLE 5

2-amino-5-chloro-benzoic acid (5 g) was reacted with SOCl$_2$ (5.2 ml) in benzene (80 ml) at the reflux temperature for 6 hours. The solution was evaporated in vacuo to dryness and the residue was dissolved in benzene (100 ml) and reacted with 2-piperidone (3.5 g) at room temperature for 40 hours. The precipitate was filtered, washed with benzene and then treated with aqueous NaHCO$_3$ to give, after filtration and washing with water until neutral, 4 g of 2-chloro-6,7,8,9-tetrahydro-11H-pyrido[2,1b]quinazoline-11-one, m.p. 121°–123° C., which was reacted with benzaldehyde (6.3 g) in methanol (100 ml) in the presence of sodium methoxide (2.75 g) under stirring at the reflux temperature for 72 hours. After cooling the reaction mixture was concentrated in vacuo, the precipitate was filtered and washed with methanol and then with water until neutral to give 4.6 g of 6-benzylidene-2-chloro-6,7,8,9-tetrahydro-11H-pyrido[2,1-b]quinazoline-11-one, m.p. 169°–170° C., NMR (CF$_3$COOD) δppm: 2.34 (m) (2H, C-8 protons), 3.25 (m) (2H, C-7 protons), 4.42 (m) (2H, C-9 protons), 7.62 (brs) (5H, phenyl protons), 7.90 (d) (1H, C-4 proton), 8.06 (brs) (1H, =CH—), 8.08 (dd) (1H, C-3 proton), 8.48 (1H) (1H, C-1 proton).

EXAMPLE 6

2-amino-benzene-1,4-dicarboxylic acid, 4-methyl ester (10 g), prepared according to Example 1, was reacted with SOCl$_2$ (9.4 ml) in dioxane (300 ml) at the reflux temperature for 3 hours. The solution was evaporated in vacuo to dryness and the residue was dissolved in dioxane (200 ml) and reacted with 2-pyrrolidinone (5.2 g) at room temperature for 36 hours. The precipitate was filtered, washed with dioxane and then treated with aqueous NaHCO$_3$ to give, after filtration and washing with water until neutral, 5.9 g of 1,2,3,9-tetrahydro-9-oxo-pyrrolo[2,1-b]quinazoline-6-carboxylic acid, methyl ester, m.p. 134°–136° C., which was reacted with benzaldehyde (3.8 g) in methanol (250 ml) in the presence of sodium methoxide (1 g) under stirring at reflux temperature for 48 hours.

After cooling the precipitate was filtered, washed with methanol and then dissolved in water: the solution was acidified with acetic acid and the precipitate was filtered, washed with water and crystallized from chloroform-ethanol to give 5 g of 3-benzylidene-1,2,3,9-tetrahydro-9-oxo-pyrrolo[2,1-b]quinazoline-6-carboxylic acid m.p. 382°–384° C., N.M.R. (CF$_3$COOD)δp.p.m.: 3.71 (bt) (2H, C-2 protons), 4.78 (t) (2H, C-1 protons), 7.72 (bs) (5H, phenyl protons), 8.31 (t) (1H, =CH—), 8.57 (dd) (1H, C-7 proton), 8.68 (d) (1H, C-8 proton), 8.71 (d) (1H, C-5 proton).

By proceeding analogously the following compounds were prepared:
3-(2-methyl-benzylidene)-1,2,3,9-tetrahydro-9-oxo-pyrrolo[2,1-b]quinazoline-6-carboxylic acid;
3-(3-methyl-benzylidene)-1,2,3,9-tetrahydro-9-oxo-pyrrolo[2,1-b]quinazoline-6-carboxylic acid.

EXAMPLE 7

2-amino-benzene-1,4-dicarboxylic acid, 4-methyl ester (10 g), prepared according to Example 1, was reacted with SOCl$_2$ (9 ml) in dioxane (300 ml) at the reflux temperature for 4 hours. The solution was evaporated to dryness and the residue was dissolved in dioxane (200 ml) and reacted with 2-piperidone (7.4 g) at room temperature for 20 hours.

The precipitate was filtered, purified with dioxane and then treated with aqueous NaHCO$_3$ to give, after filtration and washing with water until neutral, 6.6 g of 6,7,8,9-tetrahydro-11-oxo-11H-pyrido[2,1-b]quinazoline-3-carboxylic acid, methyl ester, m.p. 131°–134° C., which was reacted with benzaldehyde (5.8 g) in methanol (200 ml) in the presence of sodium methoxide (4.12 g) under stirring at the reflux temperature for 72 hours.

After cooling the precipitate was filtered and washed with methanol then it was dissolved in water: the solution was acidified with acetic acid and the precipitate was filtered, washed with water and crystallized from chloroform-ethanol to give 2.6 g of 6-benzylidene-6,7,8,9-tetrahydro-11-oxo-11H-pyrido/2,1-b/quinazoline-3-carboxylic acid, m.p. 233°–235° C., NMR (CF$_3$COOD)δp.p.m.: 2.37 (m) (2H, C-8 protons), 3.24 (t) (2H, C-7 protons), 4.43 (s) (2H, C-9 protons), 7.64 (s) (5H, phenyl protons), 8.12 (bs) (1H, =CH—), 8.45–8.75 (m) (3H; C-1, C-2 and C-4 protons).

By proceeding analogously, the following compounds were prepared:
6-(2-methyl-benzylidene)-6,7,8,9-tetrahydro-11-oxo-11H-pyrido[2,1-]quinazoline-3-carboxylic acid;
6-(3-methyl-benzylidene)-6,7,8,9-tetrahydro-11-oxo-11H-pyrido[2,1-b]quinazoline-3-carboxylic acid.

EXAMPLE 8

By proceeding according to Examples 2 and 5, starting from suitable 2-amino-benzoic acids, the following compounds were prepared:
3-benzylidene-7-methyl-1,2,3,9-tetrahydro-pyrrolo[2,1-b]quinazoline-9-one, m.p. 189°–190° C.;
6-benzylidene-2-methyl-6,7,8,9-tetrahydro-11H-pyrido[2,1-b]quinazoline-11-one;
3-benzylidene-6-chloro-1,2,3-9-tetrahydro-pyrrolo[2,1-b]quinazoline-9-one, m.p. 238°–240° C.;
3-benzylidene-5,7-dichloro-1,2,3,9-tetrahydro-pyrrolo[2,1-b]quinazoline-9-one, m.p. 216°–218° C.;
6-chloro-3-(2-methyl-benzylidene)-1,2,3,9-tetrahydro-pyrrolo[2,1-b]quinazline-9-one.

EXAMPLE 9

By proceeding according to Examples 1,6 and 8 using 5-methyl-2-pyrrolidinone, the following compounds were obtained:
3-benzylidene-1-methyl-1,2,3,9-tetrahydro-9-oxo-pyrrolo[2,1-b]quinzaoline-7-carboxylic acid, m.p. 321°–325° C.;
3-benzylidene-1-methyl-1,2,3,9-tetrahydro-9-oxo-pyrrolo[2,1-b]quinazoline-6-carboxylic acid;
3-benzylidene-7-chloro-1-methyl-1,2,3,9-tetrahydro-pyrrolo[2,1-b]quinazoline-9-one;
3-benzylidene-6-chloro-1-methyl-1,2,3,9-tetrahydro-pyrrolo[2,1-b]quinazoline-9-one;
3-benzylidene-5,7-dichloro-1-methyl-1,2,3,9-tetrahydro-pyrrolo[2,1-b]quinazoline-9-one.

EXAMPLE 10

6-N-acetyl-amino-1,2,3,9-tetrahydro-pyrrolo[2,1-b]quinazoline-9-one (1.21 g) was reacted with benzaldehyde (0.8 g) in methanol (60 g) in the presence of sodium methoxide (0.68 g) under stirring at 40° C. for 20 hours.

After cooling and acidification with acetic acid, the precipitate was filtered and washed with water: crystallization from dimethylformamide-methanol gave 0.9 g of 6-N-acetyl-amino-3-benzylidene-1,2,3,9-tetrahydro-pyrrolo[2,1-b]quinazoline-9-one, m.p. 333°–336° C., NMR (DMSO d6)δp.p.m.: 2.10 (s) (3H, —COCH$_3$), 3.21 (m) (2H, C-2 protons), 4.08 (t) (2H, C-1 protons), 7.30–7.76 (m) (7H, C-5 and C-6 protons and phenyl protons), 7.97 (d) (1H, C-8 proton), 8.09 (m) (1H, —CH=), 10.14 (bs) (1H, —NCHO—).

EXAMPLE 11

6-nitro-1,2,3,9-tetrahydro-pyrrolo[2,1-b]quinazoline-9-one, m.p. 196°–197° C. (3.7 g), prepared according to the Example 2, was reacted with benzaldehyde (2 g) in methanol (100 ml) in the presence of sodium methoxide (1.74 g) under stirring at room temperature for 16 hours and then at 60° C. for 4 hours. After concentration in vacuo of the suspension, the precipitate was filtered and washed with water until neutral: crystallization from CH$_2$Cl$_2$-methanol gave 3-benzylidene-6-nitro-1,2,3,9- tetrahydro-pyrrolo[2,1-b]quinazoline-9-one, m.p. 255°–257° C. (3.5 g), which was reacted with SnCl$_2$.2H$_2$O (25 g) in 37% HCl (15 ml) and acetic acid (45 ml) under stirring at 60° C. for 3 hours. After cooling the precipitate was filtered and washed with water and then suspended under stirring in 2.5% aqueous NaHCO$_3$: the product was filtered, washed with water until neutral and then crystallized from ethanol to give 1.6 g of 6-amino-3-benzylidene-1,2,3,9-tetrahydro-pyrrolo[2,1-b]quinazoline-9-one, m.p. 268°–270° C., NMR (DMSO-d$_6$) δppm: 3.23 (bt) (2H, C-2 protons), 4.11 (t) (2H, C-1 protons), 6.07 (bs) (2H, —NH$_2$), 6.73 (m), (2H, C-5 and C-7 protons), 7.33–7.76 (m) (5H, phenyl protons), 7.68 (bs) (1H, =CH—), 7.83 (d) (1H, C-8 proton).

By proceeding analogously the following compounds were prepared:
6-amino-3-(3,4,5-trimethoxy-benzylidene)-1,2,3,9-tetrahydro-pyrrolo[2,1-b]quinazoline-9-one, m.p. 310°–312° C.;
6-amino-3-(3,4-dichloro-benzylidene)-1,2,3,9-tetrahydro-pyrrolo[2,1-b]quinazoline-9-one, m.p. 313°–315° C.;
6-amino-3-(2-methyl-benzylidene)-1,2,3,9-tetrahydro-pyrrolo[2,1-b]quinazoline-9-one, m.p. 285°–287° C.;
6-amino-3-(3-methyl-benzylidene)-1,2,3,9-tetrahydro-pyrrolo[2,1-b]quinazoline-9-one, m.p. 265°–268° C.;
6-amino-3-(4-methyl-benzylidene)-1,2,3,9-tetrahydro-pyrrolo[2,1-b]quinazoline-9-one, m.p. 224°–227° C.;
6-amino-3-(2,5-dimethyl-benzylidene)-1,2,3,9-tetrahydro-pyrrolo[2,1-b]quinazline-9-one;
6-amino-3-(2,4-dimethyl-benzylidene)-1,2,3,9-tetrahydro-pyrrolo[2,1-b]quinazoline-9-one;
6-amino-3-(2-methoxy-benzylidene)-1,2,3,9-tetrahydro-pyrrolo[2,1-b]quinazoline-9-one, m.p. 242°–244° C.;
6-amino-3-(3-methoxy-benzylidene)-1,2,3,9-tetrahydro-pyrrolo[2,1-b]quinazoline-9-one, m.p. 267°–269° C.;
6-amino-3-(4-methoxy-benzylidene)-1,2,3,9-tetrahydro-pyrrolo[2,1-b]quinazoline-9-one, m.p. 268°–288° C.;
6-amino-3-(2,3-dimethoxy-benzylidene)-;b 1,2,3,9-tetrahydro-pyrrolo[2,1-b]quinazoline-9-one, m.p. 278°–280° C.;
6-amino-3-(2,4-dimethoxy-benzylidene)-1,2,3,9-tetrahydro-pyrrolo[2,1-b]quinazoline-9-one;
6-amino-3-(3,4-dimethoxy-benzylidene)-1,2,3,9-tetrahydro-pyrrolo[2,1-b]quinazoline-9-one;
6-amino-3-(2,5-dimethoxy-benzylidene)-1,2,3,9-tetrahydro-pyrrolo[2,1-b]quinazoline-9-one;
6-amino-3-(2-methoxy-3-ethoxy-benzylidene)-1,2,3,9-tetrahydro-pyrrolo[2,1-b]quinazoline-9-one;
6-amino-3-(3,4-dihydroxy-benzylidene)-1,2,3,9-tetrahydro-pyrrolo[2,1-b]quinazoline-9-one.
6-amino-3-(4-fluoro-benzylidene)-1,2,3,9-tetrahydro-pyrrolo[2,1-b]quinazoline-9-one, m.p. 263°–265° C.;
6-amino-3-(2-fluoro-benzylidene)-1,2,3,9-tetrahydro-pyrrolo[2,1-b]quinazoline-9-one;
6-amino-3-(2-chloro-benzyliden)-1,2,3,9-tetrahydro-pyrrolo[2,1-b]quinazoline-9-one;
6-amino-3-(3,4-methylenedioxy-benzylidene)-1,2,3,9-tetrahydro-pyrrolo[2,1-b]quinazoline-9-one, m.p. 275°–280° C.;
6-amino-3-(3-chloro-benzylidene)-1,2,3,9-tetrahydro-pyrrolo[2,1-b]quinazoline-9-one;
6-amino-3-(4-chloro-benzylidene)-1,2,3,9-tetrahydro-pyrrolo[2,1-b]quinazoline-9-one;
6-amino-3-(3-trifluoromethyl-benzylidene)-1,2,3,9-tetrahydro-pyrrolo[2,1-b]quinzaoline-9-one.

EXAMPLE 12

By proceeding according to Example 11, starting from 7-nitro-1,2,3,9-tetrahydro-pyrrolo[2,1-b]quinazoline-9-one, m.p. 196°–197° C., the following compounds were prepared:
7-amino-3-benzylidene-1,2,3,9-tetrahydro-pyrrolo[2,1-b]quinazoline-9-one, m.p. 270°–275° C., NMR (CDCl$_3$)δp.p.m.: 3.24 (m) (2H, C-2 protons), 4.13 (t) (2H, C-1 protons), 5.62 (bs) (2H, —NH$_2$), 7.00–7.70 (m) (8H, C-5 and C-6 and C-8 protons and phenyl protons), 7.56 (bs) (1H, =CH—);
7-amino-3-(2-methyl-benzylidene)-1,2,3,9-tetrahydro-pyrrolo[2,1-b]quinazoline-9-one;
7-amino-3-(3-methyl-benzylidene)-1,2,3,9-tetrahydro-pyrrolo[2,1-b]quinazoline-9-one;
7-amino-3-(4-methyl-benzylidene)-1,2,3,9-tetrahydro-pyrrolo[2,1-b]quinazoline-9-one;
7-amino-3-(2,5-dimethyl-benzylidene)-1,2,3,9-tetrahydro-pyrrolo[2,1-b]quinazoline-9-one;
7-amino-3-(2,4-dimethyl-benzylidene)-1,2,3,9-tetrahydro-pyrrolo[2,1-b]quinazoline-9-one;
7-amino-3-(2-methoxy-benzylidene)-1,2,3,9-tetrahydro-pyrrolo[2,1-b]quinazoline-9-one;
7-amino-3-(3-methoxy-benzylidene)-1,2,3,9-tetrahydro-pyrrolo[2,1-b]quinazoline-9-one;
7-amino-3-(4-methoxy-benzylidene)-1,2,3,9-tetrahydro-pyrrolo[2,1-b]quinazoline-9-one;
7-amino-3-(2,3-dimethoxy-benzylidene)-1,2,3,9-tetrahydro-pyrrolo[2,1-b]quinazoline-9-one;
7-amino-3-(2,4-dimethoxy-benzylidene)-1,2,3,9-tetrahydro-pyrrolo[2,1-b]quinazoline-9-one;
7-amino-3-(3,4-dimethoxy-benzylidene)-1,2,3,9-tetrahydro-pyrrolo[2,1-b]quinazoline-9-one;
7-amino-3-(2,5-dimethoxy-benzylidene)-1,2,3,9-tetrahydro-pyrrolo[2,1-b]quinazoline-9-one;
7-amino-3-(2-methoxy-3-ethoxy-benzylidene)-1,2,3,9-tetrahydro-pyrrolo[2,1-b]quinazoline-9-one;
7-amino-3-(3,4-dihydro-benzylidene)-1,2,3,9-tetrahydro-pyrrolo[2,1-b]quinazoline-9-one;
7-amino-3-(4-fluoro-benzylidene)-1,2,3,9-tetrahydro-pyrrolo[2,1-b]quinazoline-9-one;
7-amino-3-(2-chloro-benzylidene)-1,2,3,9-tetrahydro-pyrrolo[2,1-b]quinazoline-9-one;
7-amino-3-(3,4-methylenedioxy-benzylidene)-1,2,3,9-tetrahydro-pyrrolo[2,1-b]quinazoline-9-one;
7-amino-3-(3-chloro-benzylidene)-1,2,3,9-tetrahydro-pyrrolo[2,1-b]quinazoline-9-one;
7-amino-4-(4-chloro-benzylidene)-1,2,3,9-tetrahydro-pyrrolo[2,1-b]quinazoline-9-one.

EXAMPLE 13

2-amino-4-nitro-benzoic acid (10 g) was reacted with SOCl$_2$ (14 ml) in benzene (150 ml) at the reflux temperature for 5 hours.

After cooling the solution was evaporated in vacuo to dryness and the residue was dissolved in benzene (150 ml) and reacted with 5-methyl-2-pyrrolidinone (9 g) at room temperature for 20 hours. The precipitate was filtered, washed with isopropyl ether and then treated with aqueous 2% NaHCO$_3$ to give, after filtration and washing with water until neutral, 10 g of 1-methyl-6-nitro-1,2,3-tetrahydro-pyrrolo[2,1-b]quinazoline-9-one, m.p. 150°–152° C. (from ethyl acetate), which was reacted with benzaldehyde (7 g) in methanol (100 ml) in the presence of sodium methoxide (4.8 g) at 60° C. for 5 hours. After cooling the precipitate was filtered and washed with water and then crystallized from ethyl acetate to give 4.5 g of 3-benzylidene-1-methyl-6-nitro-1,2,3,9-tetrahydro-pyrrolo[2,1-b]quinazoline-9-one, m.p. 245°–237° C., which was reacted with SnCl$_2$.2H$_2$O (28 g) in 37% HCl (18 ml) and acetic acid (54 ml) under stirring at 60° C. for 3 hours.

After cooling the precipitate was filtered and washed with N/1 HCl and then with water and then suspended under stirring in 5% aqueous NaHCO$_3$: the product was filtered and washed with water until neutral. Crystallization from ethanol gave 7.6 g of 6-amino-3-benzylidene-1-methyl-1,2,3,9-tetrahydro-pyrrolo[2,1-b]quinazoline-9-one, m.p. 239°–241° C., NMR (DMSO d6)δp.p.m.: 1.39 (d) (3H, —CH$_3$), 2.84 (ddd) (1H, C-2 proton), 3.48 (ddd) (1H, C-2 proton), 4.73 (m) (1H, C-1 proton), 6.06 (bs) (2H, —NH$_2$), 6.69 (d) (1H, C-5 proton), 6.73 (dd) (1H, C-7 proton), 7.30–7.70 (m) (6H, =CH— and phenyl protons), 7.80 (d) (1H, C-8 proton).

By proceeding analogous the following compound was prepared:
7-amino-3-benzylidene-1-methyl-1,2,3,9-tetrahydro-pyrrolo[2,1-b]quinazoline-9-one.

EXAMPLE 14

3-nitro-6,7,8,9-tetrahydro-11H-pyrido[2,1-b]pyrimidine-11-one, m.p. 174°–177° C. (5 g), prepared according to Example 5, was reacted with benzaldehyde (3.2 g) in methanol (100 ml) in the presence of piperidine (4.2 ml) under stirring at the reflux temperature for 96 hours. After cooling the precipitate was filtered and washed with ethyl acetate: the product was purified over a SiO$_2$ column using chloroform as eluent. Crystallization from chloroform-ethanol gave 6-benzylidene-3-nitro-6,7,8,9-tetrahydro-11H-pyrido[2,1-b]pyrimidine-11-one, m.p. 207°–209° C. (4 g), which was reacted with SnCl$_2$.2H$_2$O (27 g) in 37% HCl (18 ml) and acetic acid (45 ml) under stirring at 60° C. for 4 hours. After cooling the precipitate was filtered and washed with water then was suspended under stirring in 2.5% aqueous NaHCO$_3$: the product was filtered, washed with water until neutral and purified with hot dioxane.

Crystallization from ethanol gave 0.8 g of 3-amino-6-benzylidene-6,7,8,9-tetrahydro-11H-pyrido[2,1-b]quinazoline-11-one, m.p. 190°–193° C., NMR (CDCl$_3$) δ p.p.m.: 2.02 (m) (2H, C-8 protons), 2.95 (t) (2H, C-7 protons), 4.12 (t) (2H, C-9 protons), 4.2 (bs) (2H, NH$_2$), 6.78 (dd) (1H, C-2 proton), 6.87 (d) (1H,C-4 proton), 7.3–7.6 (m), (5H,phenyl protons), 8.09 (d) (1H, C-1 proton), 8.18 (bs), (1H, —CH=).

By proceeding analogously the following compounds were prepared:
2-amino-6-benzylidene-6,7,8,9-tetrahydro-11H-pyrido[2,1-b]quinazoline-11-one;
3-amino-6-(2-methyl-benzylidene)-6,7,8,9-tetrahydro-11H-pyrido[2,1-b]quinazoline-11-one;
3-amino-6-(3-methyl-benzylidene)-6,7,8,9-tetrahydro-11H-pyrido[2,1-b]quinazoline-11-one;
3-amino-6-(4-methyl-benzylidene)-6,7,8,9-tetrahydro-11H-pyrido[2,1-b]quinazoline-11-one;
3-amino-6-(2,5-dimethyl-benzylidene)-6,7,8,9-tetrahydro-11H-pyrido[2,1-b]quinazoline-11-one;
3-amino-6-(2,4-dimethyl-benzylidene)-6,7,8,9-tetrahydro-11H-pyrido[2,1-b]quinazoline-11-one;
3-amino-6-(2-methoxy-benzylidene)-6,7,8,9-tetrahydro-11H-pyrido[2,1-b]quinazoline-11-one;
3-amino-6-(3-methoxy-benzylidene)-6,7,8,9-tetrahydro-11H-pyrido[2,1-b]quinazoline-11-one;
3-amino-6-(4-methoxy-benzylidene)-6,7,8,9-tetrahydro-11H-pyrido[2,1-b]quinazoline-11-one;
3-amino-6-(2,3-dimethoxy-benzylidene)-6,7,8,9-tetrahydro-11H-pyrido[2,1-b]quinazoline-11-one;
3-amino-6-(3,4-dimethoxy-benzylidene)-6,7,8,9-tetrahydro-11H-pyrido[2,1-b]quinazoline-11-one;
3-amino-6-(2,4-dimethoxy-benzylidene)-6,7,8,9-tetrahydro-11H-pyrido[2,1-b]quinazoline-11-one;
3-amino-6-(2,5-dimethoxy-benzylidene)-6,7,8,9-tetrahydro-11H-pyrido[2,1-b]quinazoline-11-one;
3-amino-6-(2-methoxy-3-ethoxy-benzylidene)-6,7,8,9-tetrahydro-11H-pyrido[2,1-b]quinazoline-11-one;
3-amino-6-(3,4-dihydroxy-benzylidene)-6,7,8,9-tetrahydro-11H-pyrido[2,1-b]quinazoline-11-one;
3-amino-6-(4-fluoro-benzylidene)-6,7,8,9-tetrahydro-11H-pyrido[2,1-b]quinazoline-11-one;
3-amino-6-(2-fluoro-benzylidene)-6,7,8,9-tetrahydro-11H-pyrido[2,1-b]quinazoline-11-one;
3-amino-6-(2-chloro-benzylidene)-6,7,8,9-tetrahydro-11H-pyrido[2,1b]quinazoline-11-one;
3-amino-6-(3-chloro-benzylidene)-6,7,8,9-tetrahydro-11H-pyrido[2,1-b]quinazoline-11-one;
3-amino-6-(4-chloro-benzylidene)-6,7,8,9-tetrahydro-11H-pyrido[2,1-b]quinazoline-11-one;
3-amino-6-(3,4-methylenedioxy-benzylidene)-6,7,8,9-tetrahydro-11H-pyrido[2,1-b]quinazoline-11-one.

EXAMPLE 15

3-(2-methyl-benzylidene)-1,2,3,9-tetrahydro-9-oxo-pyrrolo[2,1-b]quinazoline-7-carboxylic acid, methyl ester, m.p. 181°–183° C., (2.02 g), obtained according to Example 1, suspended in tetrahydrofuran (86 ml) was reacted with LiAlH$_4$ (0.33 g) under stirring at 0° C. for 2 hours.

After decomposition of the excess of LiAlH$_4$ by ethyl acetate, the reaction mixture was made weakly acidic by treatment with 0.1 N HCl, then the organic phase was separated and washed with water until neutral. After evaporation to dryness in vacuo, the residue was purified over a SiO$_2$ column using CHCl$_3$-methanol 50:3.5 as eluent, so obtaining 0.6 g of 7-hydroxymethyl-3-(2-methyl-benzylidene)-1,2,3,9-tetrahydro-pyrrolo[2,1-b]quinazoline-9-one, m.p. 222°–224° C., NMR (CDCl$_3$) δ ppm: 2.50 (s) (3H, —CH$_3$), 3.30 (m), (2H, C-2 protons), 4.25 (t) (2H, C-1 protons), 4.79 (bs) (2H, CH$_2$CH), 7.2–7.6 (m) (4H, phenyl protons), 7.80 (bs) (2H, C-5 and C-6 protons), 8.05 (t) (1H, =CH—), 8.22 (bs) (1H, C-8 proton).

EXAMPLE 16

3-(2-methyl-benzylidene)-1,2,3,9-tetrahydro-9-oxo-pyrrolo[2,1-b]quinazoline-7-carboxylic acid (1 g) was reacted with ethyl iodide (0.93 g) and anhydrous K$_2$CO$_3$ (0.83 g) in dimethylformamide (10 ml) under stirring at room temperature for 16 hours. After dilution with ice water the precipitate was filtered and washed with water until neutral: crystallization from chloroform-ethanol gave 0.9 g of 3-(2-methyl-benzylidene)-1,2,3,9-tetrahydro-9-oxo-pyrrolo[2,1-b]quinazoline-7-carboxylic acid, ethyl ester, m.p. 184°–185° C.

By proceeding analogously the following compounds were prepared:
3-benzylidene-1,2,3,9-tetrahydro-9-oxo-pyrrolo[2,1-b]quinazoline-7-carboxylic acid, ethyl ester;
3-(4-fluoro-benzylidene)-1,2,3,9-tetrahydro-9-oxo-pyrrolo[2,1-b]quinazoline-7-carboxylic acid, methyl ester, m;p. 264°–267° C.;
3-benzylidene-1-methyl-1,2,3,9-tetrahydro-9-oxo-pyrrolo[2,1-b]quinazoline-7-carboxylic acid, methyl ester, m.p. 217°–220° C.;

3-benzylidene-1,2,3,9-tetrahydro-9-oxo-pyrrolo[2,1-b]quinazoline-6-carboxylic acid, ethyl ester, m.p. 263°–265° C.;
6-benzylidene-6,7,8,9-tetrahydro-11-oxo-11H-pyrido[2,1-b]quinazoline-2-carboxylic acid, methyl ester, m.p. 156°–157° C.;
6-benzylidene-6,7,8,9-tetrahydro-11-oxo-11H-pyrido[2,1-b]quinazoline-3-carboxylic acid, ethyl ester;
6-(4-fluoro-benzylidene)-6,7,8,9-tetrahydro-11-oxo-11H-pyrido[2,1-b]quinazoline-2-carboxylic cid, methyl ester, m.p. 181°–184° C.;
3-(2-methyl-benzylidene)-1,2,3,9-tetrahydro-9-oxo-pyrrolo[2,1-b]quinazoline-7-carboxylic acid, methyl ester, m.p. 181°–183° C.;
3-(3-methyl-benzylidene)-1,2,3,9-tetrahydro-9-oxo-pyrrolo[2,1-b]quinazoline-7-carboxylic acid, methyl ester, m.p. 236°–238° C.;
3-(4-methyl-benzylidene)-1,2,3,9-tetrahydro-9-oxo-pyrrolo[2,1-b]quinazoline-7-carboxylic acid, methyl ester, m.p. 238°–240° C.;
3-(3-methoxy-benzylidene)-1,2,3,9-tetrahydro-9-oxo-pyrrolo[2,1-b]quinazoline-7-carboxylic acid, methyl ester, m.p. 197°–200° C.;
3-(2,4-dimethyl-benzylidene)-1,2,3,9-tetrahydro-9-oxo-pyrrolo[2,1-b]quinazoline-7-carboxylic acid, methyl ester, m.p. 235°–238° C.;
3-(2,5-dimethyl-benzylidene)-1,2,3,9-tetrahydro-9-oxo-pyrrolo[2,1-b]quinazoline-7-carboxylic acid, methyl ester, m.p. 198°–200° C.;
6-(2-methyl-benzylidene)-6,7,8,9-tetrahydro-11-oxo-11H-pyrido[2,1-b]quinazoline-2-carboxylic acid, methyl ester, m.p. 166°–169° C.;
6-(2,6-dichloro-benzylidene)-6,7,8,9-tetrahydro-11-oxo-11H-pyrido[2,1-b]quinazoline-2-carboxylic acid, methyl ester, m.p. 196°–199° C.;
6-(3-chloro-benzylidene)-6,7,8,9-tetrahydro-11-oxo-11H-pyrido[2,1-b]quinazoline-2-carboxylic acid, methyl ester, m.p. 166°–168° C.

EXAMPLE 17

By proceeding according to Example 16 the isopropyl, n-butyl and n-hexyl esters of the following compounds were prepared:
3-benzylidene-1,2,3,9-tetrahydro-9-oxo-pyrrolo[2,1-b]quinazoline-7-carboxylic acid;
3-benzylidene-1-methyl-1,2,3,9-tetrahydro-9-oxo-pyrrolo[2,1-b]quinazoline-7-carboxylic acid;
6-benzylidene-6,7,8,9-tetrahydro-11-oxo-11H-pyrido[2,1-b]quinazoline-2-carboxylic acid;
3-benzylidene-1,2,3,9-tetrahydro-9-oxo-pyrrolo[2,1-b]quinazoline-6-carboxylic acid; and
6-benzylidene-6,7,8,9-tetrahydro-11-oxo-11H-pyrido[2,1-b]quinazoline-3-carboxylic acid.

EXAMPLE 18

3-(2-methyl-benzylidene)-1,2,3,9-tetrahydro-9-oxo-pyrrolo[2,1-b]quinazoline-7-carboxylic acid (5.3 g) was reacted with SOCl2 (5.8 ml) in dioxane (120 ml) at the reflux temperature for 40 hours, then the mixture was evaporated to dryness in vacuo. The residue was treated with 250 ml of dioxane, saturated with ammonia under stirring at room temperature for 20 hours: the precipitate was filtered and washed with water until neutral. Crystallization from dimethylformamide gave 3.7 g of 3-(2-methyl-benzylidene)-1,2,3,9-tetrahydro-9-oxo-pyrrolo[2,1-b]quinazoline-7-carboxamide, m.p. 347°–349° C.; NMR (CD3COOD) δ ppm: 2.58 (s) (3H, —CH3), 3.60 (m), (2H, C-2 protons), 4.70 (m) (2H, C-1 protons), 7.3–7.8 (m), (4H, phenyl protons), 8.10 (d) (1H, C-5 proton), 8.62 (bs) (1H, =CH—), 8.68 (d d) (1H, C-6 proton), 9.17 (d) (1H, C-8 proton).

By proceeding analogously the following compounds were prepared:
3-benzylidene-1,2,3,9-tetrahydro-9-oxo-pyrrolo[2,1-b]quinazoline-7-carboxamide;
6-benzylidene-6,7,8,9-tetrahydro-11-oxo-11H-pyrido[2,1-b]quinazoline-2-carboxamide;
3-benzylidene-1,2,3,9-tetrahydro-9-oxo-pyrrolo[2,1-b]quinazoline-6-carboxamide; and
6-benzylidene-6,7,8,9-tetrahydro-11-oxo-11H-pyrido[2,1-b]quinazoline-3-carboxamide.

EXAMPLE 19

3-(2-methyl-benzylidene)-1,2,3,9-tetrahydro-9-oxo-pyrrolo[2,1-b]quinazoline-7-carboxamide (2.7 g) in dimethylformamide (100 ml) containing pyridine (2.6 ml) was reacted with p-toluenesulfonyl chloride (3.1 g) under stirring at 70° C. for 4 hours. After cooling and dilution with water, the precipitate was filtered and washed with water until neutral: crystallization from chloroform-ethanol gave 1.8 g of 7-cyano-3-(2-methyl-benzylidene)-1,2,3,9-tetrahydropyrrolo[2,1-b]quinazoline-9-one, m.p. 234°–236° C., NMR (CDCl3-DMSO-CF3COOD) δ ppm: 2.50 (s) (3H, —CH3), 3.29 (m) (2H, C-2 protons), 4.28 (t) (2H, C-1 protons), 7.30–7.60 (m) (4H, phenyl protons), 7.89 (m) (2H, C-5 and C-6 protons), 8.16 (d) (1H, C-8 proton), 8.59 (t) (1H, =CH—).

By proceeding analogously the following compounds were prepared:
7-cyano-3-benzylidene-1,2,3,9-tetrahydro-pyrrolo[2,1-b]quinazoline-9-one;
2-cyano-6-benzylidene-6,7,8,9-tetrahydro-11H-pyrido[2,1-b]quinazoline-11-one;
6-cyano-3-benzylidene-1,2,3,9-tetrahydro-pyrrolo[2,1-b]quinazoline-9-one; and
3-cyano-6-benzylidene-6,7,8,9-tetrahydro-11H-pyrido[2,1-b]quinazoline-11-one.

EXAMPLE 20

3-(2-methyl-benzylidene)-1,2,3,9-tetrahydro-9-oxo-pyrrolo[2,1-b]quinazoline-7-carboxylic acid (2 g) was reacted with thionyl chloride (2.2 ml) in dioxane (100 ml) at the reflux temperature for 24 hours, then the mixture was evaporated to dryness in vacuo. The residue was dissolved in dioxane (100 ml) and reacted with 2-diethylamino-ethanol (2.1 g) at room temperature for 48 hours. After dilution with water the precipitate was filtered, washed with water until neutral and purified over a SiO2 column using acetone-triethylamine 100:0.1 as eluent: the collected product was crystallized from ethyl acetate to give 0.9 g of 3-(2-methyl-benzylidene)-1,2,3,9-tetrahydro-9-oxo-pyrrolo[2,1-b]quinazoline-7-carboxylic acid, 2-diethylamino-ethylester, m.p. 128°–130° C., NMR (CDCl3-DMSO.d6) δ ppm: 1.10 (t)

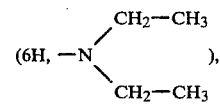

2.50 (s) (3H, —CH3), 2.69 (q)

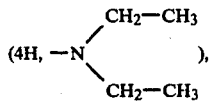

2.92 (t)

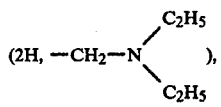

3.27 (m) (2H, C-2 protons), 4.25 (t)

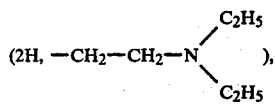

4.43 (t) (2H, C-1 protons), 7.2–7.6 (m) (4H, phenyl protons), 7.78 (d) (1H, C-5 proton), 8.05 (t) (1H, =C—), 8.33 (dd) (1H, C-6 proton), 8.88 (d) (1H, C-8 proton).

By proceeding analogously the following compounds were prepared:

3-benzylidene-1,2,3,9-tetrahydro-9-oxo-pyrrolo[2,1-b]quinazoline-7-carboxylic acid, 2-diethylaminoethyl ester;

3-(4-fluoro-benzylidene)-1,2,3,9-tetrahydro-9-oxo-pyrrolo[2,1-b]quinazoline-7-carboxylic acid, 2-diethylamino ethyl ester;

3-benzylidene-1-methyl-1,2,3,9-tetrahydro-9-oxo-pyrrolo[2,1-b]quinazoline-7-carboxylic acid, 2-diethylamino-ethyl ester;

3-benzylidene-1,2,3,9-tetrahydro-9-oxo-pyrrolo[2,1-b]quinazoline-6-carboxylic acid, 2-diethylaminoethyl ester, m.p. 125°–130° C., N.M.R. (CDCl₃) δ p.p.m.: 1.10 (t)

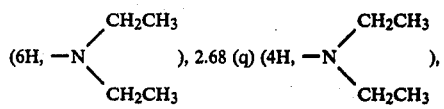

2.91 (t) (2H, —COOCH₂CH₂N<), 3.23 (dt) (2H, C-2 protons), 4.24 (bt) (2H, C-1 protons), 4.45 (t) (2H, —COOCH₂CH₂N<), 7.2–7.6 (m) (5H, phenyl protons), 7.80 (t) (1H, —CH=), 7.96 (dd) (1H, C-7 proton), 8.25 (d) (1H, C-8 proton), 8.34 (d) (1H, C-5 proton);

6-benzylidene-6,7,8,9-tetrahydro-11-oxo-11H-pyrido[2,1-b]quinazoline-3-carboxylic acid, 2-diethylamino-ethyl ester.

EXAMPLE 21

3-benzylidene-1,2,3,9-tetrahydro-9-oxo-pyrrolo[2,1-b]quinazoline-7-carboxylic acid was treated with the stoichiometric amount of sodium methoxide in methanol at 60° C. for 10 minutes. After concentration in vacuo to a small volume, the precipitate was filtered and washed with a little cold methanol and then with hexane: 3-benzylidene-1,2,3,9-tetrahydro-9-oxo-pyrrolo[2,1-b]quinazoline-7-carboxylic acid, sodium salt, m.p. >300° C., was obtained.

By proceeding analogously the following compounds were prepared:

3-(2-methyl-benzylidene)-1,2,3,9-tetrahydro-9-oxo-pyrrolo[2,1-b]quinazoline-7-carboxylic acid, sodium salt;

3-benzylidene-1-methyl-1,2,3,9-tetrahydro-9-oxo-pyrrolo[2,1-b]quinazoline-7-carboxylic acid, sodium salt;

3-benzylidene-1,2,3,9-tetrahydro-9-oxo-pyrrolo[2,1-b]quinazoline-6-carboxylic acid, sodium salt;

6-benzylidene-6,7,8,9-tetrahydro-11-oxo-11H-pyrido[2,1-b]quinazoline-3-carboxylic acid, sodium salt.

EXAMPLE 22

6-amino-3-benzylidene-1,2,3,9-tetrahydro-pyrrolo[2,1-b]quinazoline-9-one (0.6 g), prepared according to Example 11, dissolved in dimethylformamide (30 ml) was reacted with acetic anhydride (2 ml) in presence of pyridine (1 ml) at room temperature for 20 hours.

The reaction mixture was diluted with ice/water and the precipitate was filtered and washed with water: crystallization from dimethylformamide-methanol gave 0.4 g of 6-N-acetyl-amino-3-benzylidene-1,2,3,9-tetrahydro-pyrrolo[2,1-b]quinazoline-9-one, m.p. 333°–336° C., N.M.R. (DMSO d6) δ p.p.m.: 2.10 (s) (3H, —COCH₃), 3.21 (m) (2H, C-2 protons), 4.08 (t), (2H, C-1 protons), 7.30–7.76 (m) (7H, C-5 and C-7 protons and phenyl protons), 7.97 (d) (1H, C-8 proton), 8.09 (m) (1H, —CH=), 10.14 (bs) (1H, —NH—).

By proceeding analogously the following compounds were prepared:

3-benzylidene-6-N-formyl-amino-1,2,3,9-tetrahydropyrrolo[2,1-b]quinazoline-9-one;

7-N-acetyl-amino-3-benzylidene-1,2,3,9-tetrahydropyrrolo[2,1-b]quinazoline-9-one;

3-N-acetyl-amino-6-benzylidene-6,7,8,9-tetrahydro-11H-pyrido[2,1-b]quinazoline-11-one;

2-N-acetyl-amino-6-benzylidene-6,7,8,9-tetrahydro-11H-pyrido[2,1-b]quinazoline-11-one.

EXAMPLE 23

Tablets, each weighing 200 mg and containing 100 mg of the active substance are manufactured as follows:

| Composition (for 10.000 tablets) | |
|---|---|
| 3-benzylidene-1,2,3,9-tetrahydro-9-oxo-pyrrolo[2,1-b]quinazoline-6-carboxylic acid | 1000 g |
| lactose | 710 g |
| corn starch | 237.5 g |
| talc powder | 37.5 g |
| magnesium stearate | 15 g |

The 3-benzylidene-1,2,3,9-tetrahydro-9-oxo-pyrrolo[2,1-b]quinazoline-6-carboxylic acid, lactose and a half of the corn starch are mixed; the mixture is then forced through a sieve of 0.5 mm openings. Corn starch (18 g) is suspended in warm water (180 ml). The resulting paste is used to granulate the powder. The granules are dried, comminuted on a sieve of a sieve size 1.4 mm, then the remaining quantity of starch, talc and magnesium stearate is added, carefully mixed, and processed into tablets using punches of 8 mm diameter.

We claim:

1. A compound of general formula (I)

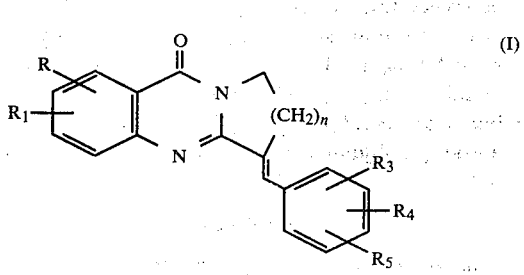

wherein n is 1 or 2;

R is hydrogen; and $R_1$ is a carboxy group or a group —$COOR_6$, wherein $R_6$ represents a $C_1$–$C_6$ alkyl group which may be unsubstituted or substituted by $C_1$–$C_4$ dialkylamino group; $R_2$ represents a hydrogen atom or a $C_1$–$C_4$ alkyl group; each of $R_3$, $R_4$ and $R_5$ independently represents a hydrogen or a halogen atom, a hydroxy group, formyloxy, a $C_2$–$C_8$ alkanoyloxy group, a —$CF_3$ group, a $C_1$–$C_4$ alkyl group, a $C_1$–$C_4$ alkoxy group or a $C_3$–$C_4$ alkenyloxy group or adjacent groups represented by two of $R_3$, $R_4$ and $R_5$, taken together, form a $C_1$–$C_3$ alkylenedioxy group; and the pharmaceutically acceptable salts thereof.

2. A compound of formula (I) according to claim 1 wherein:

n is 1 or 2; R is hydrogen; $R_1$ is a carboxy, $C_1$–$C_4$ alkoxycarbonyl, or di($C_1$–$C_2$ alkyl)-amino-ethoxycarbonyl; $R_2$ is hydrogen or methyl; each of $R_3$, $R_4$ and $R_5$ independently represents hydrogen, $C_1$–$C_2$ alkyl, $C_1$–$C_3$ alkoxy, fluorine, chlorine or adjacent groups represented by two of $R_3$, $R_4$ and $R_5$, taken together, form a methylenedioxy group; and the pharmaceutically acceptable salts thereof.

3. A salt of a compound of claim 1, wherein the salt is the sodium salt of a carboxylic acid.

4. A salt of a compound of claim 1, wherein the salt is the hydrochloride of a basic ester thereof.

5. A compound according to claim 4, wherein the basic ester is the 2-diethyl-amino-ethanol ester.

6. A $C_1$–$C_6$ alkyl ester of a compound of claim 1, wherein the $C_1$–$C_6$ alkyl group is methyl, ethyl, isopropyl, n-butyl and n-hexyl.

7. A compound selected from the group consisting of:
3-(2-methyl-benzylidene)-1,2,3,9-tetrahydro-9-oxo-pyrrolo[2,1-b]quinazoline-7-carboxylic acid;
3-(3-methyl-benzylidene)-1,2,3,9-tetrahydro-9-oxo-pyrrolo[2,1-b]quinazoline-7-carboxylic acid;
3-(2-methyl-benzylidene)-1,2,3,9-tetrahydro-9-oxo-pyrrolo[2,1-b]quinazoline-6-carboxylic acid;
3-benzylidene-1-methyl-1,2,3,9-tetrahydro-9-oxo-pyrrolo[2,1-b]quinazoline-7-carboxylic acid;
3-benzylidene-1-methyl-1,2,3,9-tetrahydro-9-oxo-pyrrolo[2,1-b]quinazoline-6-carboxylic acid;
6-(2-methyl-benzylidene)-6,7,8,9-tetrahydro-11-oxo-11H-pyrido[2,1-b]quinazoline-2-carboxylic acid;
6-(2-methyl-benzylidene)-6,7,8,9-tetrahydro-11-oxo-11H-pyrido[2,1-b]quinazoline-3-carboxylic acid;
and the pharmaceutically acceptable salts and the $C_1$–$C_6$ alkyl esters thereof.

8. A compound selected from the group consisting of:
3-benzylidene-1,2,3,9-tetrahydro-9-oxo-pyrrolo[2,1-b]quinoline-6-carboxylic acid, ethyl ester;
3-benzylidene-1,2,3,9-tetrahydro-9-oxo-pyrrolo[2,1-b]quinazoline-6-carboxylic acid, 2-diethylaminoethyl ester;
6-benzylidene-6,7,8,9-tetrahydro-11-oxo-11H-pyrido[2,1-b]quinazoline-3-carboxylic acid, ethyl ester, and
the pharmaceutically acceptable salts thereof.

9. 3-benzylidene-1,2,3,9-tetrahydro-9-oxo-pyrrolo[2,1-b]quinazoline-7-carboxylic acid and the pharmaceutically acceptable salts and the $C_1$–$C_6$ alkyl esters thereof.

10. 3-benzylidene-1,2,3,9-tetrahydro-9-oxo-pyrrolo[2,1-b]quinazoline-6-carboxylic acid and the pharmaceutically acceptable salts and the $C_1$–$C_6$ alkyl esters thereof.

11. 6-benzylidene-6,7,8,9-tetrahydro-11-oxo-11H-pyrido[2,1-b]quinazoline-2-carboxylic acid and the pharmaceutically acceptable salts and the $C_1$–$C_6$ alkyl esters thereof.

12. 6-benzylidene-6,7,8,9-tetrahydro-11-oxo-11H-pyrido[2,1-b]quinazoline-3-carboxylic acid and the pharmaceutically acceptable salts and the $C_1$–$C_6$ alkyl esters thereof.

13. A pharmaceutical composition suitable for the treatment of or the prevention of the formation of gastrointestinal ulcers, comprising a therapeutically effective amount of a compound of formula (I) as claimed in claim 1, or a pharmaceutically acceptable salt thereof, in association with a suitable carrier or diluent.

14. A method for the treatment of or prevention of the formation of gastrointestinal ulcers in a patient in need of such treatment, said method comprising administering to said patient a therapeutically effective amount of a compound of the formula (I) as claimed in claim 1, or a pharmaceutically acceptable salt thereof.

* * * * *

UNITED STATES PATENT AND TRADEMARK OFFICE
CERTIFICATE OF CORRECTION

PATENT NO. : 4,428,952

DATED : January 31, 1984

INVENTOR(S) : Doria et al

It is certified that error appears in the above—identified patent and that said Letters Patent is hereby corrected as shown below:

Columns 1 and 23, formula (I) the $R_2$ substituent is missing, replace as below:

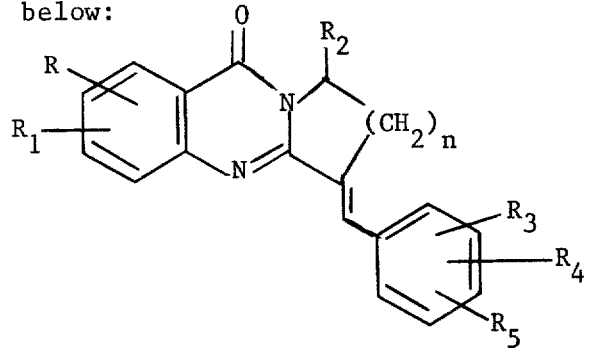

Column 1, line 27, "$R_2$" is to be deleted and replaced by --$R_1$--

Column 24, line 15 delete "quinoline" and replace by --quinazoline--

Signed and Sealed this

Nineteenth Day of February 1985

[SEAL]

Attest:

DONALD J. QUIGG

Attesting Officer       Acting Commissioner of Patents and Trademarks